(12) United States Patent
Virno et al.

(10) Patent No.: US 10,576,039 B2
(45) Date of Patent: Mar. 3, 2020

(54) OPHTHALMIC FORMULATION COMPRISING CITICOLINE CARRIED BY LIPOSOME FOR THE TREATMENT OF GLAUCOMA

(71) Applicant: Omikron Italia S.r.l., Rome RM (IT)

(72) Inventors: Cristiano Virno, Rome RM (IT); Marco Malizia, Rome (IT)

(73) Assignee: Omikron Italia S.r.l., Rome (IT)

( * ) Notice: Subject to any disclaimer, the term of this patent is extended or adjusted under 35 U.S.C. 154(b) by 0 days.

(21) Appl. No.: 16/342,261

(22) PCT Filed: Oct. 16, 2017

(86) PCT No.: PCT/IB2017/056400
§ 371 (c)(1),
(2) Date: Apr. 16, 2019

(87) PCT Pub. No.: WO2018/073720
PCT Pub. Date: Apr. 26, 2018

(65) Prior Publication Data
US 2019/0321292 A1    Oct. 24, 2019

(30) Foreign Application Priority Data
Oct. 17, 2016    (IT) .................. 102016000103956

(51) Int. Cl.
*A61K 9/127*    (2006.01)
*A61K 47/18*    (2017.01)
*A61K 47/36*    (2006.01)
*A61P 27/06*    (2006.01)
*A61K 9/00*    (2006.01)
*A61K 31/7068*    (2006.01)
*A61K 9/08*    (2006.01)

(52) U.S. Cl.
CPC ............ *A61K 9/127* (2013.01); *A61K 9/0048* (2013.01); *A61K 9/08* (2013.01); *A61K 31/7068* (2013.01); *A61K 47/18* (2013.01); *A61K 47/36* (2013.01); *A61P 27/06* (2018.01)

(58) Field of Classification Search
None
See application file for complete search history.

(56) References Cited

FOREIGN PATENT DOCUMENTS

| EP | 0114577 A1 * | 8/1984 | ............. A61K 9/127 |
| WO | WO-2010092597 A2 * | 8/2010 | ............ A61K 9/0019 |
| WO | WO-2011101802 A1 * | 8/2011 | ............ A61K 9/0048 |

* cited by examiner

*Primary Examiner* — Nannette Holloman
(74) *Attorney, Agent, or Firm* — Sterne, Kessler, Goldstein & Fox P.L.L.C.

(57) ABSTRACT

The present invention relates to an ophthalmic formulation comprising citicoline and liposomes to be used in treating glaucoma. The inventors have found that the liposomes result to be particularly effective in carrying citicoline in the posterior segment of the eye (vitreous chamber) and in reaching the retina and the optic nerve head.

21 Claims, 2 Drawing Sheets

OPHTHALMIC FORMULATION COMPRISING CITICOLINE CARRIED BY LIPOSOME FOR THE TREATMENT OF GLAUCOMA

The present invention relates to an ophthalmic formulation comprising liposomes containing citicoline or salts thereof and the use thereof in treating glaucoma. The inventors have found that the liposomes result to be extremely effective in carrying citicoline in the posterior segment of the eye (vitreous chamber) and in reaching the retina and optic nerve head.

STATE OF PRIOR ART

Glaucoma is a chronic neurodegenerative pathology characterized by progressive loss of retinal ganglion cells and structural changes in the optic nerve head. It represents the second leading cause of blindness worldwide and thus it is a very felt problem. The most common form, open-angle primary glaucoma, has as main risk factor the increase in intraocular pressure (IOP) therefore the first therapeutic approach is represented by hypotonizing topical drugs. However, since more than one-third of the patients, despite being under good pressure control, delay yet do not stop vision damage progression, other non pressure-dependent mechanisms are deemed to be involved (Grieb P et al. J Neurosci Res 2002). Specifically, following a primary insult of hyperbaric nature, neuron apoptosis is triggered, which interferes with normal blood supply at the level of the capillary district of this structure, and regular axonal transport, anterograde as well as retrograde, of metabolites and neurotrophins indispensable for ganglionar cell survival is compromised. Apoptosis is accountable for the secondary insult linked to local excitotoxicity mechanisms due to hyperstimulation of NMDA receptors by glutamate freed from apoptotic cells. Glutamate, in fact, when present in excessive concentrations in the extracellular space hyperstimulates NMDA receptors on the surface of the surrounding neurons, which cause the opening of $Ca^{++}$ channels. Hyperafflux of $Ca^{++}$ ions in the cell represents the trigger of the biochemical cascade that will lead to apoptosis of the neuron itself, configuring a mechanism capable of self-feeding also in the absence of primary insult. Another key step in the cell damage mechanism in the course of apoptosis is represented by hyperactivation of phospholipase A2, an enzyme able to destabilize and disgregate the cell membrane through catabolism of its main constituent, the phosphatidylcoline phospholipid (Burgoyne F C et al. Prog Retin Eye Res 2005; 24). Evidently, ocular hypotonization has scanty effects on the secondary insult representing a real death cascade accountable for damage progression.

In the neuroprotection field, particular interest is addressed to the citicoline (cytidine-5'-diphosphocholine) molecule, for its action mechanism and the scientific evidence going from experimental studies to clinical trials on glaucomatous patients. Citicoline (cytidine-5'-diphosphocholine) is a natural precursor of phosphatidylcholine, main component of neuronal and mitochondrial membranes. Taken orally, it is rapidly absorbed and less than 1% of it is excreted in the feces. Plasma peak is reached 1 hour after ingestion, followed by a larger peak 24 h later. It is metabolized in the intestinal wall and in the liver. Coline and citidine deriving from hydrolysis of the same molecule are absorbed by systemic circulation and separately cross the blood-brain barrier (BEE) for resynthesis into citicoline (cytidine-5'-diphosphocholine) at the brain level. Elimination mostly occurs via the respiratory route and urinary excretion, mirroring the two plasma peaks, i.e. first rapid elimination, followed by a slower one (Citicoline, monograph Altern Med Rev 2008).

At the brain level citicoline mainly acts as substrate for phosphatidylcholine formation and as phospholipase A2 inhibitor, therefore having a direct action on the membrane damage of the still viable neuron. Moreover, this molecule exhibits a neuromodulating action mainly at the level of the dopaminergic system, which offers the rationale for citicoline use in treating Parkinson's disease, as well as glaucoma, dopamine being one of the main neurotransmitters involved in the transmission of the visual signal both at a retinal and post-retinal level.

Numerous studies in literature demonstrate the positive effect of citicoline on glaucomatous patients, both on the visual field, by computerized campimetry, (Pecori Giraldi et al 1989) and on the entire visual pathway, by use of pattern electroretinogram (PERG) and visual evoked potentials (PEV) (Parisi et al 1999, 2005, 2008, Rejadak et al 2003).

In particular, the studies by Parisi and collaborators confirm the same results in glaucomatous patients under hypotonizing therapy and with citicoline administered both intramuscularly (1000 mg/die) and orally (1600 mg/die), with respect to glaucomatous patients under hypotonizing therapy only, and the need to cyclically repeat the treatment in order to maintain the positive effects on the visual function (overall study time, 8 years).

In 2009, Chan et al. published the results of in vivo use of magnetic resonance spectroscopy (proton magnetic resonance spectroscopy $^{1}H$ MRS) on experimental models of glaucoma in rat, demonstrating that glaucoma is also characterized by alteration of coline metabolism at the level of the visual cortex, mirroring the compromission of the structural integrity of the neuronal membranes. Intramuscular administration of citicoline for treating glaucoma is clearly very uncomfortable for the patient and it does not allow use of the substance over the long periods needed to have the positive results observed by the studies. Intramuscular administration, besides the discomfort of not being self-done and the entailed need for patients to have a person capable of doing intramuscular injections available, need that, above all in aged patients, might be hard to meet, can expose to the risk of infective complications following chronic therapy.

Oral administration of citicoline for treating glaucoma, though representing a step forward with respect to intramuscular therapy, is conditioned by the difficulties due to the impossibility of use in subjects having gastric or intestinal pathologies, as well as by the low concentration of active principle arriving at the level of the optic nerve head, the nervous structure mostly damaged by glaucoma pathology owing to metabolization in the liver.

Oshitari et al. (Neuroreport 2002) evaluated the neurite regeneration effect in vitro obtained by adding Citicoline to cultured retinal ganglion cells (RGCs) obtained from explanted mouse retinas.

The patent EP2538918 filed by the same inventors describes as preferred embodiment an ophthalmic formulation comprising citicoline, hyaluronic acid and benzalchonium chloride for topical use in treating glaucoma. The hyaluronic acid increases the residence time at the level of anatomo-functional ocular surface/lacrimal film unit, allowing to increase everywhere the drug/eye contact time; benzalchonium chloride (BAK) further favours the drug transcorneal passage thanks to the temporary and reversible weakening of the corneal epithelium barrier: the stimulation of the corneal gap junctions allows citicoline to pass in vitreous chamber and to spread through the vitreous humour and the uveoscleral routes, as far as the retinal ganglion cells and the optic nerve head. The final effect is then to maximize the transportation of the active principle towards the therapeutic target. However, it is believed that BAK could cause for chronic use, in time, a slight cytotoxicity at the level of the corneal epithelium, above all in determined types of patients (ex. patients with sever ocular dryness) and in particular following a continuous use as it happens in case of chronic pathologies such as glaucoma.

SUMMARY OF THE INVENTION

Studies performed by the present inventors on an in vivo experimental model surprisingly demonstrated that administration on the ocular surface of an ophthalmic formulation comprising citicoline incorporated in the liposomes is ideal to ensure the passage of the active principle in the posterior segment of the eye (vitreous chamber) and in reaching the retina and optic nerve head. The inventors have found that the use in ophthalmic formulation of citicoline incorporated in liposomes allows to carry the active principle at a high efficiency even in absence of BAK and thickening agents such as the hyaluronic acid. The present invention then has the advantage of not having to use BAK in the formulation to carry effectively the active principle towards its target.

Moreover the experimental results obtained by the inventors and described in the experimental section of the present description have surprisingly highlighted that:
- the solution of citicoline suitably carried with liposomes succeeds in crossing the corneal barrier and in reaching the posterior segment of the eye (vitreous chamber);
- the formulation of citicoline in liposomes is capable of penetrating the vitreous humour with a high concentration. In prior art it was necessary to use both a thickening agent such the hyaluronic acid in combination with a penetration enhancer such as BAK;
- the quantity of citicoline detected in the blood flow is extremely reduced (and it is very complex to determine the concentration thereof), therefore it is possible to exclude a systemic effect of citicoline;
- the formulation of citicoline in liposomes resulted to be particularly stable in time. The advantages, the features and use modes of the present invention will be made apparent from the following detailed description of some embodiments thereof, given by way of example and not for limitative purposes.

DETAILED DESCRIPTION OF THE INVENTION

Figure 1A:
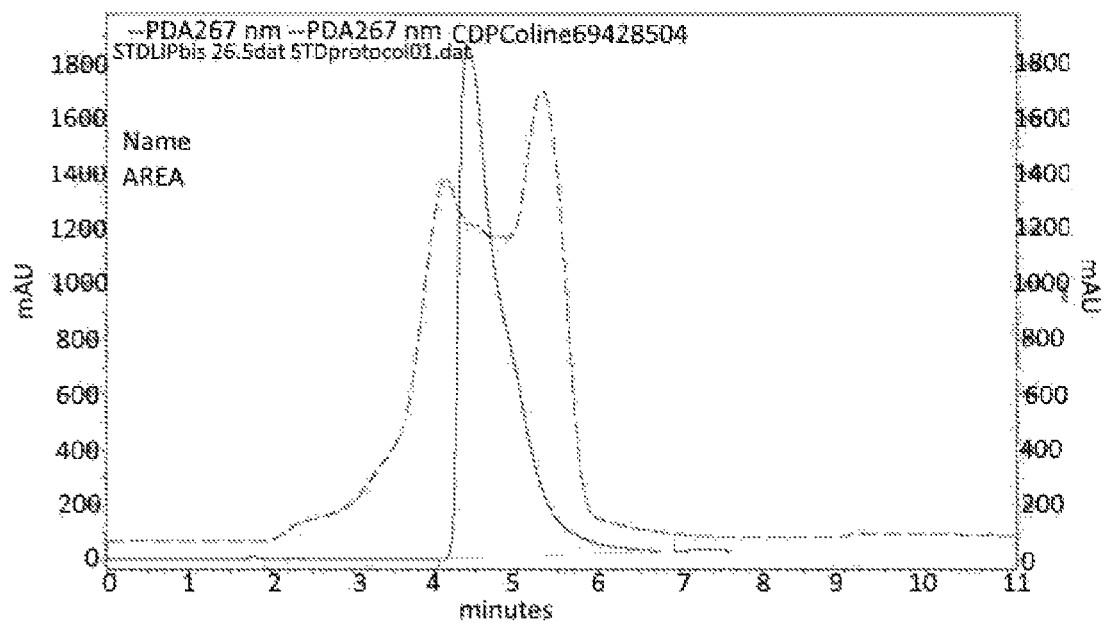
FIG. 1A. HPLC elution profile obtained by analysing a standard sample of citicoline and a standard sample of citicoline incorporated in liposomes.

The present invention relates to an ophthalmic formulation comprising liposomes containing citicoline or salts thereof and the use thereof in treating glaucoma. The composition of the present invention could be used in treating all different forms of glaucoma such as for example congenital glaucoma, open-angle glaucoma, closed-angle glaucoma and glaucoma without hypertension.

In the present description under the term liposomes phospholipidic vesicles with nanometric sizes are meant, preferably such liposomes consist of a phospholipidic double layer. In the compositions according to the present description citicoline is incorporated inside the liposomes so as to be suitably carried. According to an embodiment the liposomes' sizes will be between 25 nm and 1 μm, preferably between 25 nm and 200 nm, still more preferably between 100 and 150 nm. According to a preferred embodiment such liposomes will consist of a phospholipidic double layer of hydrogenated phospholipids.

Such compositions of course could further comprise one or more carriers, diluents and/or excipients suitable for preparing ophthalmic compositions. All carriers, diluents or excipients tolerated by the eye are suitable for preparing ophthalmic compositions. The compositions could further include hyaluronic acid and/or stearylamine. The hyaluronic acid, in particular the one having high molecular weight, thanks to the mucoadhesive and mucomimetic properties, allows to increase the residence time at the level of anatomofunctional ocular surface/lacrimal film unit, and thus to increase drug/eye contact time. The stearylamine is a molecule able to further improve the ocular adhesion of the solution and which could then favour a greater absorption of citicoline.

According to the present invention citicoline (cytidine-5'-diphosphocholine) used in the compositions or salts thereof such as for example the mono-sodium salt could be purchased or prepared according to the protocols described in the known art such as for example Kyowa production protocol (Drug Master File citicoline Kyowa Haakko Kogyo Co., Ltd). The concentration of citicoline in said compositions preferably is comprised in the range between 5 and 30 mg per gram or ml of composition. According to the invention citicoline is preferably used at a concentration per unit dose between about 0.0035 and about 1.5 mg/die. Under "unit dose" the dose is meant that is administered each time to the patient, both divided into plural administrations during the day, and daily, and at intervals of days. The herein described compositions could comprise, besides citicoline, other active principle for topical use in treating glaucoma like e.g. topical antihypertensive drugs.

Said compositions for topical use could be in any form deemed suitable by the person skilled in the art to be applied directly on the ocular surface, like e.g solution, ointment, suspension, eye drops, gel, cream, foam, spray, ointment. The eye drops may comprise salts such as sodium phosphate monobasic monohydrate, sodium phosphate bibasic dodecahydrate, sodium chloride or a combination thereof, preferably it may be a physiological solution with 0.9% NaCl, at a physiological pH (pH 7.0-7.4) and a physiological osmolarity (280-300 mOsm/kg). In a preferred embodiment the eye drops comprises citicoline between 0.5% and 3% (% p/p) preferably 2%. The present description even provides a method for the treatment of glaucoma comprising the administration of effective amounts of a composition as described herein to patients who require it. In the treatment method the exact dosage and the frequency for administering the compositions will depend upon the particular severity of the condition to be treated, upon age, weight and general physical conditions of the particular patient, as it is well known to those skilled in the art. Some effective doses that can be administered are mentioned hereinafter: they could be administered at a unit dose comprised between about 0.0035 and about 1.5 mg/die optionally in combination with one or more compounds for the treatment of glaucoma like e.g. topical antihypertensive drugs the unit dose thereof could be about 100%, about 90%, about 80%, about 70%, about 60%, about 50%, about 40%, about 30% or less with respect to the unit doses commonly used in therapy against glaucoma.

The present invention also relates to a method for preparing the herein described ophthalmic compositions comprising the following steps of:
a) mixing the lipids solubilised with citicoline;
b) concentrating the mixture by evaporation;
c) rehydrating the mixture concentrated at step b) into an aqueous solution;
c) submitting to high-pressure extrusion the mixture of step b).

the method could include an additional step of sterilization by means of filtration at 0.2 micron.

The invention will be described in details hereinafter in the following examples which have a purely illustrative purpose without limiting the granted protection scope.

EXAMPLES

Example 1. Formula A

Hydrogenated Liposomes/2.0% Citicoline/0.075% Hyaluronic Acid

| Percentage composition | | |
|---|---|---|
| Raw materials | % p/p | |
| Citicoline monosodium salt | 2.000 | Active principle |
| Phospholipids 90H | 2.000 | Hydrogenated phospholipids very stable to oxidation, white colour |
| Sodium phospate bibasic dodecahydrate | 0.685 | Buffer System |
| Sodium phosphate monobasic dehydrate | 0.225 | Buffer System |
| Sodium chloride | 0.246 | Isotony modulator |
| Hyaluronic acid sodium salt | 0.075 | Mucoadhesive thickener |
| Water as required | 100 | |

| Formulation property | | |
|---|---|---|
| | Acceptance limits | Results |
| pH | 7-7.4 | 7.19 |
| Osmolality (mOsmol/kg) | 280-300 | 289 |
| Average diameter (µm) | <0.2 | <0.2 |
| Sterile by filtration at 0.2 micron | | Yes compliant |

Example 2. Formula B

Hydrogenated Liposomes with 2.0% Stearylamine/Citicoline/0.075% Hyaluronic acid

| Percentage composition | | |
|---|---|---|
| Raw materials | % p/p | |
| Citicoline monosodium salt | 2.000 | Active principle |
| Phospholipids 90H | 2.000 | Hydrogenated phospholipids very stable to oxidation, white colour |
| Stearylamine | 0.005 | Positive charge modulator |
| Sodium phospate bibasic dodecahydrate | 0.685 | Buffer System |
| Sodium phosphate monobasic dehydrate | 0.225 | Buffer System |
| Sodium chloride | 0.246 | Isotony modulator |
| Hyaluronic acid sodium salt | 0.075 | Mucoadhesive thickener |
| Water as required | 100 | |

| Formulation property | | |
|---|---|---|
| | Acceptance limits | Results |
| pH | 7-7.4 | 7.19 |
| Osmolality (mOsmol/kg) | 280-300 | 289 |
| Average diameter (µm) | <0.2 | <0.2 |
| Sterile by filtration at 0.2 micron | | Yes compliant |

Example 3

Preparation of the Composition Comprising Citicoline Incorporated in the Liposomes In a glass flask the lipids (phospholipids 90H) and the pulverized active principle, i.e. citicoline, are solubilized with a mixture of organic solvents. Then, the solution is under vacuum evaporated by means of a rotavapor, until the formation of a film, which once formed is further left under vacuum to remove the last traces of solvents. Subsequently the lipidic film is rehydrated, with a suitable solution (water, buffer, etc.). The mixture is then made to stir until assuming a homogeneous appearance, without precipitates. The formation of Multi Lamellar Vesicles (MLV) is then obtained. The mixture of phospholipids and active principle after being hydrated and suitably mixed is subjected to high-pressure extrusion, this causes the formation of liposomes and the decrease in the sizes thereof. The number of extrusion cycles modifies the sizes of the liposomes which then can reach a size equal or smaller than 200 nm, by making the liposomes sterilizable by filtration at 0.2 micron.

Experimental Data

For the experimental group 12 animals were used for an adequate statistical management of the results (average, standard deviation and significance).

The used number of animals, following statistical evaluation, represents the minimum number therefrom it is possible to obtain significant data. In the study male mice of Wistar-Kyoto strain were used according to previous experiments performed by the research group.

The animals were kept and manipulated in a structure suitable for keeping the animals under optimum conditions (temperature, humidity, ventilation, hygienic conditions). In the study a formulation in solution for ophthalmic use was utilized constituted by 200-mm liposomes including 2% citicoline sodium salt. In particular, the preparation composition is the following one (in g/100 g of solution):
Citicoline monosodium salt 2.0
Phospholipids 90 H 2.0
Sodium phosphate bibasic bihydrate 0.685
Sodium phosphate monobasic dihydrate 0.225
Sodium chloride 0.246

The experiment was carried out on 12 male mice (weight of each mouse about 250 g) so divided:
a) 4 mice were treated with liposomes both eyes (mice 1-2-3-4);

b) 4 mice were treated with liposomes right eye only (5-6-7-8);
c) 4 control mice (mouse 9-10-11-12);

The treatment provides the instillation with 2 gt of liposome solution twice a day for three days. On the fourth day, after sacrificing the animal, their eyes will be collected, rinsed in physiological solution and so kept on ice:
a. Mice 1-2-3-4 both whole eyes in PBS solution.
b. Mice 5-6-7-8 whole Right Eye (RE) treated in PBS solution separated from the Left Eye (Le) still dipped in PBS.
c. Mice 9-10-11-12 both whole eyes in PBS solution.

Moreover on each animal an endocardial blood sample was taken after total anaesthesia both before and after treatment, just before being sacrificed, by using a test tube with EDTA; on such sample, for each animal, the blood count and citicoline presence were determined.

In laboratory with a vacuum sucking system connected to a 100-µL syringe the vitreous humour was taken diluted with 50 µL of a solution 0.6 M of perchloric acid to remove the possible presence of proteins and brought to the final volume of 150 µL. The sample was then neutralized with potassium carbonate and treated with 150 µL of chloroform to remove possible traces of lipidic substances.

After extraction and subsequent centrifugation at 13,000 rpm for 5 minutes at 5° C. the supernatant was taken and injected into a HPLC system equipped with a ultraviolet detector Diode Array and chromatographic column C18—Kromasil 250×4.6 mm with 5-µm particles. Of course, all samples, even the checks, were subjected to the same kind of treatment before being analysed in HPLC.

As far as the blood is concerned, after having carried out the blood count 500 µL of suspension were deproteinized with perchloric acid, neutralized and extracted with chloroform and, after centrifugation at 13,000 rpm for 5 minutes, analysed in HPLC.

Results

Figure 1B:
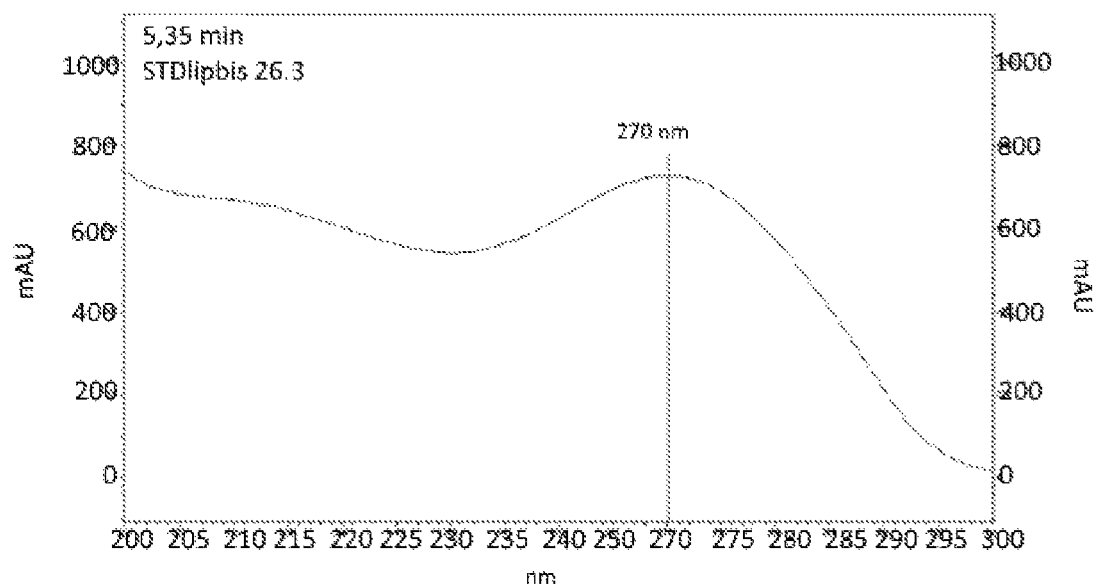
FIG. 1B. Absorption spectrum obtained by analysing a standard sample of citicoline incorporated in liposomes.

The mice were treated for 3 days by topical route with the liposome formulation. In order to determine a reference standard, the features of 2% citicoline suspension (weight/Volume concentration) before treatment were determined by HPLC; the results are shown in FIG. 1 both as to HPLC elution profile (FIG. 1A) and the absorption spectrum (FIG. 1B). Based upon such elements the quantity of citicoline, existing both in vitreous humour and in blood, is determined.

At the end of the treatment none of the animals showed behaviour anomalies or cutaneous or ocular systemic lesions.

Figure 2:
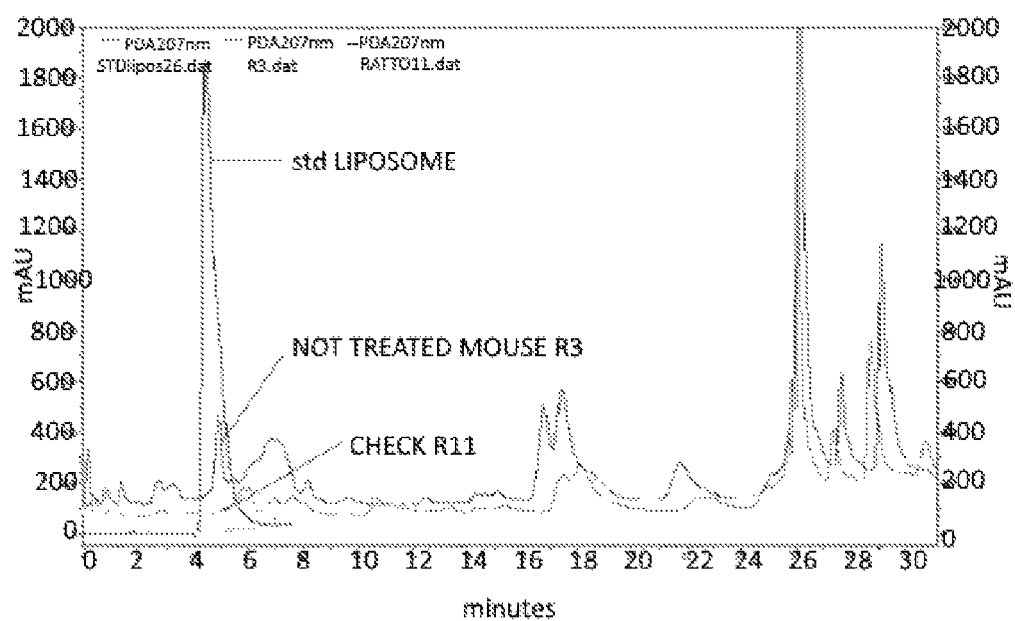
FIG. 2. HPLC elution profile of FIG. 2 shows that citicoline is present in high concentrations only in the vitreous humour from eyes of the animals treated topically, whereas the vitreous humour in the not treated eyes does not show any trace of citicoline.

The obtained results showed that:
1) Citicoline is present, in an average concentration (weight/Volume) of 0.065 g (±0.01)% (corresponding to 13% of the amount applied topically), only in the vitreous humour from the eyes treated topically, whereas the vitreous humour of the not treated eyes does not show any trace of citicoline (FIG. 2).
2) The amount of citicoline existing in the blood is much lower than the one existing in the vitreous humour and it is difficult to determine the concentration thereof (weight/Volume) (resulting about 0.01 g (±0.002)%), since in some cases such quantity is below the system detection sensitivity.

In conclusion, the eye drops in the liposome formulation results to be able to to penetrate in higher extent in the vitreous humour with respect to what observed if administered in solution (Parisi et al., 2015; Roberti et al., 2015) (reaching a concentration (weight/volume) of about 0.07 g (±0.01) %) (at the ocular level it is a high concentration).

The invention claimed is:

1. A composition for ophthalmic use comprising liposomes that include citicoline or salts thereof.
2. The composition according to claim 1 wherein said liposomes comprise a double layer of phospholipids and an aqueous core.
3. The composition according to claim 1 wherein said liposomes are composed of hydrogenated phospholipids.
4. The composition according to claim 1 further comprising hyaluronic acid and/or stearylamine.
5. The composition according to claim 1 wherein said citicoline has a concentration between 0.5 and 3% by weight.
6. The composition according to claim 1 which is a solution, ointment, suspension, eye drops, gel, cream, foam, spray, or ointment.
7. The composition according to claim 1 which has a pH between 7 and 7.4 and an osmolarity between 280 and 300 mOsml/kg.
8. The composition according to claim 1 wherein said liposomes have a size between 25 nm and 1 µm.
9. The composition according to claim 1 further comprising one or more active agents for topical use in treating glaucoma.
10. The composition according to claim 1 wherein the composition does not comprise benzalchonium chloride (BAK).
11. A composition for ophthalmic use comprising liposomes, hyaluronic acid, and/or stearylamine, wherein the liposomes include citicoline or salts thereof.
12. The composition according to claim 11 wherein said liposomes comprise a double layer of phospholipids and an aqueous core.
13. The composition according to claim 11 wherein said liposomes consist of hydrogenated phospholipids.
14. The composition according to claim 11 wherein the composition does not contain benzalchonium chloride (BAK).
15. The composition according to claim 11 wherein said citicoline has a concentration between 0.5 and 3% by weight.
16. The composition according to claim 11 which is a solution, ointment, suspension, eye drops, gel, cream, foam, spray, or ointment.
17. The composition according to claim 11 which has a pH between 7 and 7.4 and an osmolarity between 280 and 300 mOsml/kg.
18. The composition according to claim 11 wherein said liposomes have a size between 25 nm and 1 µm.
19. The composition according to claim 11 further comprising one or more active agents for topical use in treating glaucoma.
20. The composition for use according to claim 9 wherein said agents are topical anti-hypertensive drugs.
21. A method of treating glaucoma in a subject in need thereof comprising topically administering a pharmaceutically effective amount of the composition of claim 1 to said subject.

* * * * *